US009220679B2

(12) United States Patent
Pardina Palleja et al.

(10) Patent No.: US 9,220,679 B2
(45) Date of Patent: Dec. 29, 2015

(54) TRANSVAGINAL PHOSPHODIESTERASE INHIBITORS FOR INFERTILITY TREATMENT

(75) Inventors: Maria Carmen Pardina Palleja, Barcelona (ES); Miguel Angel Vaz-Romero Uña, Barcelona (ES)

(73) Assignee: PROKREA BCN, S.L., Barcelona (ES)

( * ) Notice: Subject to any disclaimer, the term of this patent is extended or adjusted under 35 U.S.C. 154(b) by 0 days.

(21) Appl. No.: 14/128,953

(22) PCT Filed: Jun. 20, 2012

(86) PCT No.: PCT/ES2012/070453
§ 371 (c)(1),
(2), (4) Date: Feb. 20, 2014

(87) PCT Pub. No.: WO2012/175775
PCT Pub. Date: Dec. 27, 2012

(65) Prior Publication Data
US 2014/0194448 A1    Jul. 10, 2014

(30) Foreign Application Priority Data
Jun. 23, 2011 (ES) .................................. 201131059

(51) Int. Cl.
| A61K 31/497 | (2006.01) |
| A61K 31/52 | (2006.01) |
| A61K 31/44 | (2006.01) |
| A61K 31/415 | (2006.01) |
| A61K 31/40 | (2006.01) |
| A61K 9/00 | (2006.01) |
| A61K 9/06 | (2006.01) |
| A61K 31/437 | (2006.01) |
| A61K 31/444 | (2006.01) |
| A61K 31/522 | (2006.01) |
| A61K 47/32 | (2006.01) |
| A61K 45/06 | (2006.01) |

(52) U.S. Cl.
CPC ................. *A61K 9/0034* (2013.01); *A61K 9/06* (2013.01); *A61K 31/40* (2013.01); *A61K 31/437* (2013.01); *A61K 31/444* (2013.01); *A61K 31/522* (2013.01); *A61K 45/06* (2013.01); *A61K 47/32* (2013.01)

(58) Field of Classification Search
CPC . A61K 9/0034; A61K 31/416; A61K 31/435; A61K 31/44; A61K 31/52
USPC .................. 514/252.16, 263.1, 334, 406, 408
See application file for complete search history.

(56) References Cited

U.S. PATENT DOCUMENTS 2,914,563 A * 11/1959 Allen et al. ................... 564/324

FOREIGN PATENT DOCUMENTS

| DE | 19801438 A1 | 7/1999 |
| EP | 1473034 A1 | 11/2004 |
| WO | 9962533 A1 | 12/1999 |
| WO | 2004/087211 A2 | 10/2004 |
| WO | 2005/027939 A1 | 3/2005 |

OTHER PUBLICATIONS

Paulus, W.E. et al., "Benefit of Vaginal Sildenafil Citrate in Assisted Reproduction Therapy," Fertility and Sterility, Apr. 2002, vol. 77, No. 4, pp. 846-847.

* cited by examiner

*Primary Examiner* — Kevin E Weddington
(74) *Attorney, Agent, or Firm* — Rothwell, Figg, Ernst & Manbeck P.C.

(57) ABSTRACT

The present invention relates to a new application of phosphodiesterase inhibitors for couple infertility treatment which forms an effective alternative to the invasive assisted reproductive techniques such as conjugal artificial insemination and which consists of the transvaginal administration of a phosphodiesterase inhibitor immediately before and/or after coitus. It also relates to dosage forms suitable for the intravaginal administration of phosphodiesterase inhibitors.

26 Claims, No Drawings

TRANSVAGINAL PHOSPHODIESTERASE INHIBITORS FOR INFERTILITY TREATMENT

CROSS-REFERENCE OF THE RELATED APPLICATION

The present application is a 35 U.S.C. §371 National Phase Entry Application of PCT/ES2012/070453, filed 20 Jun. 2012, designating the United States, which in turn claims priority to Spanish Patent Application No. P 201131059, filed on 23 Jun. 2011, both of which are incorporated herein by reference.

TECHNICAL FIELD

The present invention relates to an alternative to the invasive assisted reproductive techniques for infertility treatment by administrating a phosphodiesterase inhibitor transvaginally.

STATE OF THE PRIOR ART

In developed countries it is calculated that approximately 15% of the couples wishing to conceive a child have difficulties for achieving same. A couple is considered infertile if the couple was incapable of conceiving after having unprotected sexual relationships for at least 12 months. As described, for example, in the document by Dohle et al., *Guidelines on Male Infertility* (*update* 2010) published by the European Association of Urology, it is estimated that a male infertility factor is found in approximately 50% of the infertile couples. Male infertility is mainly caused by poor semen quality due to causes which may be very heterogeneous therefore, in practice, the cause of male infertility is often unknown and is often referred to as idiopathic infertility. In these cases, an empirical medical treatment can be resorted to but said treatments tend to be long with varying effectiveness and are always accompanied by the risk of side effects associated with any prolonged oral pharmacological treatment. Therefore, it is often considered that the best option for these couples is to resort to assisted reproductive techniques in attempt to have offspring.

Assisted reproductive techniques which infertile couples tend to resort to are conjugal artificial insemination (CAI) and in vitro fertilization (IVF). CAI consists of inseminating the semen of the couple itself previously subjected to a sperm capacitation process by intrauterine route so that the sperm acquire the ovule fertilizing capacity. IVF is based on extracting oocytes from the woman and fertilizing them in vitro with sperm from the partner which are also previously capacitated.

Even though the assisted reproductive techniques have become a very common practice in our society over the last decades they still have a series of drawbacks.

First, assisted reproductive techniques are invasive techniques which necessarily require medical intervention to achieve conception and which can be troublesome for couples, beside the fact that, inevitably, pregnancy stops being the result of spontaneous sexual intercourse between a couple. Furthermore, said techniques have a high cost and a moderate percentage of success. Therefore, the article by Hernández et al., Registro de IAC-IAD de la Sociedad Espanôla de Fertilidad (CAI-AID Register of the Spanish Society of Fertility). Year 2003, Revista Iberoamericana de Fertilidad y Reproducción Humana (Iberoamerican Magazine of Human Fertility and Reproduction), 2007, 24 (4): 229-240, for example, compiles the data from insemination registers (conjugal artificial insemination CAI and artificial insemination by donor or AID) collected by the Spanish Society of Fertility in 2003 from the data supplied by 95 centers throughout Spain, and it is observed that for couple insemination or CAI, the pregnancy rate is 14.7%. For the above reasons, it is found that many couples are reluctant to undergo the assisted reproductive techniques.

Within the scope of assisted reproductive techniques, the state of the art describes the in vitro use of pentoxifylline, a non-specific phosphodiesterase enzyme inhibitor, for the treatment of sperm samples due to its sperm motility improving capacity for the purpose of improving the capacitation of sperm intended to be used in said techniques either for in vitro fertilization or for artificial insemination, as described, for example, in the article by Minhas et al., *Effectiveness of pentoxifylline in semen preparation for intrauterine insemination*, Hum. Reprod., 1996, 11 (6): 1236-9.

Likewise, the in vitro effect of selective phosphodiesterase PDE1 and PDE4 inhibitors in sperm extracts has also been studied. Selective PDE4 inhibitors increase sperm motility whereas selective PDE1 inhibitors stimulate acrosome reaction, such as described in the article by Fisch et al., *Enhancement of motility and acrosome reaction in human spermatozoa: differential activation by type specific phosphodiesterase inhibitors*, Hum. Reprod. 1998; 13 (5): 1248-54.

On the other hand, the article by Aparicio et al., *Pentoxifylline (BL 191) by oral administration in the treatment of asthenozoospermia*, Andrology, 1980, 12 (3): 228-31, describes the oral administration of pentoxifylline for treating men with asthenozoospermia or low sperm motility. Said article describes a study where a high dose of pentoxifylline was administrated to a group of 15 infertile men with asthenozoospermia, 1200 mg daily for four months. A substantial improvement in sperm motility of the subjects treated was observed, and 2 pregnancies (13.3%) were counted after the treatment. However, treatment with oral pentoxifylline, as typically occurs with any continuous pharmacological treatment, entails a certain risk of adverse effects, particularly, among other possible side effects, it has been described that pentoxifylline can induce hypotension and arrhythmias. Spanish Patent Application ES-A-2245609 describes that pentoxifylline or its metabolites can cause mutagenic effects.

International Patent Application WO-A-2004/037262 describes the transvaginal administration of phosphodiesterase inhibitors for the purpose of stimulating female sexual desire.

Therefore, there is still a need to provide an alternative for treating couple infertility, simple to use and non-invasive, respecting couple intimacy and the natural conception process, while being effective, safe and economical.

OBJECT OF THE INVENTION

The object of the invention is the use of a phosphodiesterase inhibitor for preparing a medicament intended for the transvaginal treatment of couples with infertility.

Another object of the invention is a phosphodiesterase inhibitor for use in the transvaginal treatment of couples with infertility.

Another object of the invention is a pharmaceutical composition of a phosphodiesterase inhibitor.

Another object of the invention is a kit including the composition of a phosphodiesterase inhibitor.

DETAILED DESCRIPTION OF THE INVENTION

The purpose of the present invention is to provide a phosphodiesterase inhibitor administered transvaginally for use in treatment of couples with infertility.

The authors of the present invention have developed a new use for phosphodiesterase inhibitors through transvaginal administration, which is significantly effective for infertility treatment, providing a safe, economical and easy-to-use treatment, whereby it forms an efficient and non-invasive alternative to the assisted reproductive methods.

Phosphodiesterase Inhibitors

Phosphodiesterase inhibitors are a group of drugs which inhibit the action of the enzymes from the family of cyclic-nucleotide phosphodiesterases (PDEs) that catalyze the hydrolysis of the inner phosphate bond of the cyclic monophosphate nucleotides cAMP (cyclic adenosine monophosphate) and cGMP (cyclic guanosine monophosphate). Thus Phosphodiesterase inhibitors act inhibiting the metabolism of second intercellular messengers cAMP and cGMP.

The family of phosphodiesterases is made up of 11 groups sequentially known as phosphodiesterase 1 (PDE1) to phosphodiesterase 11 (PDE11). Such drugs are selective inhibitors, i.e., drugs specifically inhibiting some of said groups, as well as other drugs which are known as non-specific or non-selective phosphodiesterase inhibitors, i.e., drugs simultaneously inhibiting more than one phosphodiesterase, have been described.

Within the scope of the present invention, the term phosphodiesterase inhibitors includes any inhibitory drug of said group of enzymes and it encompasses both non-specific phosphodiesterase inhibitors and selective inhibitors of any of the phosphodiesterases PDE1, PDE2, PDE3, PDE4, PDE5, PDE6, PDE7, PDE8, PDE9, PDE10 or PDE11, as well as mixtures of more than one phosphodiesterase inhibitor.

Among the selective inhibitors suitable for use in the scope of the present invention are, for example, selective phosphodiesterase 1 (PDE1) inhibitors such as, for example, vinpocetine; selective phosphodiesterase 2 (PDE2) inhibitors such as, for example, EHNA (erythro-9-(2-hydroxy-3-nonyl) adenine); selective phosphodiesterase 3 (PDE3) inhibitors such as, for example, milrinone, amrinone, enoxymone, cilostazol or cylostamide; selective phosphodiesterase 4 (PDE4) inhibitors such as, for example, rolipram, denbufylline, cilomilast and roflumilast; or selective phosphodiesterase 5 (PDE5) inhibitors such as, for example, sildenafil, tadalafil or vardenafil, even though the latter also interact with phosphodiesterase 6 since PDE5 and PDE6 are structurally related.

Among the non-specific inhibitors suitable for use in the scope of the present invention are, for example, pentoxifylline, theophylline, theobromine, ibudilast, papaverine, and 3-isobutyl-1-methylxanthine, among others.

In a preferred embodiment of the invention, the phosphodiesterase inhibitor is selected from the group consisting of a phosphodiesterase 1 (PDE1) inhibitor, a phosphodiesterase 3 (PDE3) inhibitor, a phosphodiesterase 4 (PDE4) inhibitor and a non-selective phosphodiesterase inhibitor, and a combination thereof.

In a more preferred embodiment, the phosphodiesterase inhibitor is selected from the group consisting of pentoxifylline, rolipram, milrinone and ibudilast.

In a particularly preferred embodiment of the invention, the phosphodiesterase inhibitor is pentoxifylline.

Rolipram is the international non-proprietary name (INN) designating the product 4-(3-cyclopentyloxy)-4-methoxyphenyl)-2-pyrrolidinone which is a selective phosphodiesterase 4 (PDE4) inhibitor.

Rolipram can be prepared, for example, as described in the Belgian patent BE-A-826923.

Milrinone is the international non-proprietary name (INN) designating the product 1,6-dihydro-2-methyl-6-oxo-(3,4'-bipyridine)-5-carbonitrile which is a selective phosphodiesterase 3 (PDE3) inhibitor.

Milrinone can be prepared, for example, as described in the Belgian patent BE-A-886336.

Ibudilast is the international non-proprietary name (INN) designating the product 2-methyl-1-(2-(1-methyethyl)pyrazolo(1,5-a)pyridin-3-yl)-1-propanone. It is a non-specific phosphodiesterase inhibitor inhibiting phosphodiesterases 3, 4, 10 and 11.

Ibudilast can be prepared, for example, as described German patent DE-A-2315801.

Pentoxifylline is the international non-proprietary name (INN) designating the product 3,7-dihydro-3,7-dimethyl-1-(5-oxohexyl)-1H-purine-2,6-dione, a drug belonging to the group of xanthines, particularly methylxanthines.

Pentoxifylline has been marketed for years to treat peripheral arterial diseases and circulatory disorders due to its haemorheological properties capable of reducing blood viscosity and thus improving peripheral blood circulation and enhancing venous return.

Likewise, it is known that pentoxifylline has a pharmacological action as a non-specific phosphodiesterase inhibitor, capable of inhibiting phosphodiesterases PDE1-5, such as described, for example, in the article by Meskini et al. *Phosphodiesterase inhibitory profile of some related xanthine derivatives pharmacologically active on the peripheral microcirculation.* Biochem. Pharmacol. 1994; 47 (5): 781-8.

Pentoxifylline can be prepared, for example, as described in the U.S. Pat. No. 3,422,107.

In the context of the present invention, phosphodiesterase inhibitor is understood in a broad term and includes, in each case, its possible pharmaceutically acceptable salts and/or solvates.

Particularly, for example, the names rolipram, milrinone, ibudilast and pentoxifylline also include their possible salts and/or solvates.

The phosphodiesterase inhibitor according to the present invention is not administered according to a pre-established chronic administration guideline, but according to a prompt treatment concomitantly with sexual intercourse, preferably at the time of maximum female fertility.

The dose of the phosphodiesterase inhibitor administered transvaginally according to the present invention is comprised between 200 mg and 800 mg of pentoxifylline in each administration, preferably comprised between 300 mg and 600 mg, more preferably comprised between 350 mg and 450 mg, and yet more preferably 400 mg of pentoxifylline.

Infertility

Couple fertility is defined as the couple capacity of having healthy offspring through normal sexual activity.

In contrast, couple infertility is defined as the coupled incapacity for conceiving a child after attempting to do so for a certain determined time period.

According to the definition by WHO (World Health Organization), infertility is the inability of a sexually active couple who does not use contraceptive methods to achieve pregnancy within one year period. Within the scope of reproductive medicine, this period is usually reduced to 6 months when the woman is 35 years old or more.

It is estimated that a male infertility factor is found in approximately 50% of infertile couples. Male infertility is mostly caused by certain anomalies in semen characteristics even though at times it is also attributed to other causes such as, for example, an anomaly or obstruction in the genital tract, or an erectile or sexual dysfunction.

In the scope of the present invention, male infertility or infertility of male origin refers to the infertility due to the existence of some anomaly in semen characteristics, such as a low sperm content (oligozoospermia), low sperm motility (asthenozoospermia or asthenospermia), an abnormal morphology (teratozoospermia), or a combination of the effects above (oligoasthenoteratozoospermia).

In the scope of the present invention, the expression "treatment of couples with infertility" refers to the infertility treatment of sexually active couples who do not use contraceptive methods and who have not achieved pregnancy after a time period considered as normal, usually 1 year or 6 months as defined previously; or to the treatment of couples in which the male has been diagnosed with male infertility due to having an anomaly in the semen, regardless of the time elapsed since attempt to conceive is made.

In a preferred embodiment of the present invention, the use of the phosphodiesterase inhibitor is indicated for the treatment of couples with infertility substantially caused by male infertility, more preferably due to an anomaly in the semen characteristics, and yet more preferably due to asthenozoospermia.

In the scope of this invention, the term "treatment" applied to the couples with infertility or to infertility, refers to the attempt to remedy the effect caused by said infertility, and it specifically refers to the couples' attempt to achieve a pregnancy and father offspring.

Likewise, in the scope of this invention, the term "infertility" is considered equivalent to the terms "sterility" or "subfertility".

The authors of the present invention have surprisingly confirmed that a high percentage of pregnancies are achieved by means of the transvaginal administration of phosphodiesterase inhibitory drugs in woman. Therefore, for example, as observed in the results of a study with pentoxifylline described in Example 3, after the transvaginal administration of pentoxifylline, a pregnancy percentage of 20% was achieved in couples with infertility substantially caused by male infertility. This percentage of success is significantly higher than that obtained by conjugal artificial insemination (14.7%) and even higher compared with that described for the oral administration of pentoxifylline (13.3%), with the additional advantage of it being a simpler and non-invasive method which does not cause any type of allergy or side effect and which also maintains and even improves the characteristics of cervical mucus.

In general, couples with infertility susceptible to being treated with phosphodiesterase inhibitors according to the present invention are couples who are candidates to be subjected to an assisted reproductive technique either by conjugal artificial insemination or by in vitro fertilization and who do not wish to undergo any of said invasive techniques.

The use of phosphodiesterase inhibitors according to the present invention is an advantageous option with respect to the assisted reproductive techniques, since it is a non-invasive self-administration treatment respecting couple intimacy, and allowing conceiving naturally after sexual intercourse without altering the spontaneity of coitus. Furthermore, this treatment is more economical that the assisted reproductive techniques.

After performing a microscopic examination of the cervical exudate or mucus of women treated with pentoxifylline transvaginally, after 15 and 20 hours from product administration, an improvement in sperm quality in terms of motility is observed both in the case of asthenozoospermia and in the case of normospermia, a significant number of type A sperm according to the WHO classification, i.e., sperm with rectilinear movement at a speed greater than 25 μm/s being counted.

Likewise, said examination reveals an improvement in the characteristics of cervical mucus in terms of its transparency, filancia (filament-forming capacity) and a leukocytic diathesis, even when is an adverse day of the genital cycle, or even when the woman is under treatment with ovulation inducing drugs which negatively alter the properties of cervical mucus.

Another object of the invention is a method for treating couples with infertility comprising the administration of phosphodiesterase inhibitors to the woman by intravaginal route.

According to the use of this invention, the phosphodiesterase inhibitor, in the form of a suitable pharmaceutical composition, must be introduced in the vaginal cavity. The administration is performed associated with sexual intercourse, preferably coinciding with the days of maximum female fertility, and can be administered before and/or after coitus, preferably immediately before or immediately after coitus, although a fraction of the composition can be administered before coitus and another fraction after, preferably, immediately before and immediately after coitus. In the case of administrating the composition of phosphodiesterase inhibitor in two fractions, the fraction administered before coitus is comprised between 5% and 50% with respect to the total dose applied and the fraction administered immediately after coitus is comprised between 50% and 95% with respect to the total dose applied.

In the context of the invention, the term "immediately" refers to a time period not more than 30 minutes, preferably not more than 15 minutes, and yet more preferably not more than 5 minutes.

After coitus and after applying the product, the woman preferably remains in supine position for at least one hour.

To obtain greater treatment effectiveness, it is advisable to perform the treatment on the days of maximum female fertility. This can be performed in a self-controlled manner by the couples, for example, through their knowledge of the menstrual cycle or through the observation of the characteristics of vaginal mucus as an indicator of the more fertile days. In contrast, the most fertile days can also be determined by means of a vaginal ultrasound.

The gel can be administered in 3 different cycles or in several days of the same cycle.

In another embodiment of the invention, the phosphodiesterase inhibitor can be administered in combination with an ovulation-inducing drug. Ovulation-inducing drugs include, for example, clomiphene, human gonadotropins, or human recombinant gonadotropins.

In another embodiment of the invention, the transvaginal phosphodiesterase inhibitor can be used as a complement to the artificial insemination technique for the purpose of increasing the chance of success thereof, i.e., of increasing the chance of achieving pregnancy. In this case, a specific amount of the composition containing the phosphodiesterase inhibitor, preferably a semi-solid composition in the form of cream, ointment, or gel is applied in any of the cupolas occluding the uterine cervix after having performed the intrauterine insemination. The semi-solid composition of the phosphodiesterase inhibitor sometimes act as an occlusive stopper occluding those sperm which would be lost in the plastic cupola, while at the same time allows the reactivation thereof to move upwards again towards the endometrial cavity. In another embodiment, an amount of the pharmaceutical composition containing the phosphodiesterase inhibitor is placed at the vaginal fundus and the use of plastic cupolas in the uterine cervix is disregarded.

Transvaginal Compositions of Phosphodiesterase Inhibitors

An object of the present invention is a pharmaceutical composition for transvaginal administration comprising a phosphodiesterase inhibitor and at least one pharmaceutically acceptable excipient for use in the treatment of couples with infertility.

In a preferred embodiment, the pharmaceutical composition comprises a phosphodiesterase inhibitor which is selected from the group consisting of a phosphodiesterase 1 (PDE1) inhibitor, a phosphodiesterase 3 (PDE3) inhibitor, a phosphodiesterase 4 (PDE4) inhibitor and a non-selective phosphodiesterase inhibitor, and a combination thereof.

In a more preferred embodiment, the pharmaceutical composition comprises a phosphodiesterase inhibitor which is selected from the group consisting of pentoxifylline, rolipram, milrinone and ibudilast.

In a particularly preferred embodiment, the pharmaceutical composition comprises pentoxifylline.

In the context of the present invention, the term "transvaginal administration" is considered equivalent to "intravaginal administration" or "vaginal administration", and refers to the application of the drug inside the vagina, typically several centimeters therein and it is preferably as deep as possible inside the vagina.

Most transvaginal dosage forms need an auxiliary device or an applicator to achieve deep insertion as is already well known by the person skilled in the art.

The pharmaceutically acceptable forms for transvaginal administration include solid forms, such as ovules, vaginal suppositories or vaginal tablets, as well as semi-solid forms such as creams, gels, ointments, pastes or foams, or in general any type of aqueous or non-aqueous suspension or emulsion. Said pharmaceutical forms are prepared by mixing, dissolving or dispersing the phosphodiesterase inhibitor in a pharmaceutically acceptable diluent carrier, and optionally adding at least one excipient which is also pharmaceutically acceptable for intravaginal administration, according to the methods known by the person skilled in the art, and as described, for example, in the pharmaceutical technology manual *Remington The Science and Practice of Pharmacy*, $20^a$ edition, Lippincott, Williams & Wilkins, Philadelphia, 2000 [ISBN: 0-683-306472]. The carriers and/or excipients suitable for preparing these pharmaceutically acceptable forms suitable for transvaginal administration are described, for example, in the book by R. C. Rowe et al., *Handbook of Pharmaceutical Excipients*, $4^a$ edition, Pharmaceutical Press, London, 2003 [ISBN: 0-85369-472-9].

Therefore, for example, carriers suitable for preparing the vaginal tablets include lactose, sucrose, glucose, mannitol, sorbitol, cellulose or cellulose derivatives, among others, or a combination thereof. The vaginal tablets preferably contain a disintegrating agent, and are more preferably formulated with an effervescent base with carbonates and an organic acid, such as citric acid or tartaric acid, for example.

The vaginal suppositories and vaginal ovules can be prepared, for example, with carriers such as glycerin, cocoa butter, a glycerol-gelatin mixture, polyethylene glycol, polyethylene oxide, or solid fats, such as for example, the commercial products known as Witepsol® made up of the mixtures of triglycerides, diglycerides and monoglycerides, among others, or with a mixture thereof.

Creams, as is well known by the person skilled in pharmaceutical technology, are semi-solid emulsions which can be oil-in-water (o/w) type or water-in-oil (w/o) type, formulated from an oily phase, an aqueous phase and an emulsifying agent. The oily phase is made up of a carrier which can be, for example, liquid paraffin or plant oil such as, for example, castor oil, almond oil, peanut oil, sesame oil, of cotton seed oil or corn oil.

Ointments are semi-solid fat preparations containing the dissolved active ingredient or are in the form of dispersion. Ointments can be formulated with various carriers such as paraffin, plastibases (mixture of polyethylene with a series of hydrocarbons), plant oils, such as for example, peanut oil, sesame oil, olive oil, cotton seed oil, almond oil, corn oil, silicones or polyethylene glycols, among others, or with a mixture thereof. Pastes are prepared similarly to ointments and they have a more solid consistency due to that they contain higher amount of insoluble solid substances.

Foams are prepared according to methods well known by the person skilled in the art, usually by preparing a suspension of the active substance in a suitable carrier, preferably a plant or semi-synthetic oil, in the presence of a thickening agent and subsequently putting said suspension in a recipient closed with a valve through which a propellant is introduced.

Gels are obtained from a liquid which is gelled by adding a rheologic agent or a gelling agent. Some gelling agents suitable for use in the present invention are, for example, carrageenan, guar gum, tragacanth, locust bean gum, pectin, agar, alginic acid, methylcellulose, hydroxyethylcellulose, hydroxypropyl methylcellulose, carboxymethylcellulose, carbomers, and polyethylene glycol, among others.

Gels can be hydrophobic which are also known as oleogels, in which the carrier tends to be liquid paraffin or an oil; or hydrophilic, in which the carrier is water, a water soluble monohydroxy or polyhydroxy alcohol, or a hydroalcoholic mixture.

In the scope of this invention, gels, particularly hydrophilic gels prepared preferably from a combination of water with a polyhydroxy alcohol are particularly preferred.

Another object of the present invention is a pharmaceutical composition in the form of hydrophilic gel for transvaginal administration comprising a phosphodiesterase inhibitor, polyhydroxy alcohol, water, carbomer and alkaline agent.

The phosphodiesterase inhibitor is preferably selected from the group consisting of a phosphodiesterase 1 (PDE1) inhibitor, a phosphodiesterase 3 (PDE3) inhibitor, a phosphodiesterase 4 (PDE4) inhibitor and a non-selective phosphodiesterase inhibitor, and a combination thereof; more preferably, the phosphodiesterase inhibitor is selected from the group consisting of pentoxifylline, rolipram, milrinone and ibudilast; yet more preferably, the phosphodiesterase inhibitor is pentoxifylline.

In a preferred embodiment, the composition consists essentially of a phosphodiesterase inhibitor, polyhydroxy alcohol, water, carbomer, alkaline agent and preservative.

The authors of the present invention have developed a composition of a phosphodiesterase inhibitor for transvaginal administration in the form of hydrophilic gel comprising a mixture of water and a polyhydroxy alcohol as the carrier, a carbomer as the gelling agent and an alkaline agent. This composition can be advantageously applied for the treatment of couples with infertility.

The polyhydroxy alcohol is an alcohol containing more than one hydroxyl group and for preparing the composition of the invention selection can be made from the group consisting of propylene glycol, dipropyleneglycol, glycerin, 1,2,6-hexanetriol, sorbitol, polyethylene glycol 100 (PEG100), polyethylene glycol 200 (PEG200), polyethylene glycol 300 (PEG300) and polyethylene glycol 400 (PEG400). Propylene glycol is preferably selected as the polyhydroxy alcohol.

A preferred gelling agent are carbomers which, as is well known by the person skilled in the art, are cross-linked acrylic acid polymers. Cross-linking agents include sucrose allyl ether and pentaerythritol allyl ether.

Particularly preferred are carbomers aqueous solution, at 0.5% by weight/volume and at a pH value comprised between 6 and 11, of which has a viscosity comprised between 25000 and 700000 mPa·s. Among the carbomers which comply with this characteristic are carbomer 934, carbomer 934P and carbomer 940, sharing registration number CAS 9003-01-4. These products are commercially available under the names Carbopol® 934, Carbopol® 934P or Carbopol® 940. The most preferred carbomer is carbomer 940, in aqueous solution, at 0.5% by weight/volume and at a pH value comprised between 6 and 11, which has a viscosity comprised between 40000 and 60000 mPa·s.

It is well know that carbomers form acid colloidal dispersions when they are dispersed in water having a pH value comprised between 2.5 and 3.5, being necessary to neutralize them with an alkaline agent so that they acquire gel consistency. The alkaline agent is preferably selected from the group consisting of L-lysine, L-arginine, borax, potassium hydroxide, sodium hydroxide, ammonia, sodium bicarbonate, aminomethylpropanol, tetrahydroxypropylethylenediamine, tromethamine, ethoxylated cocoamine (cocamine PEG15), diisopropanolamine, triisopropanolamine, and triethanolamine. More preferably triethanolamine is used.

A preferred pharmaceutical composition for intravaginal administration according to the present invention is a gel comprising a phosphodiesterase inhibitor, propylene glycol, carbomer, triethanolamine and water.

A particularly preferred pharmaceutical composition is a gel consisting essentially of a phosphodiesterase inhibitor, propylene glycol, carbomer, triethanolamine, water and preservative.

A preferred pharmaceutical composition comprises a phosphodiesterase inhibitor in a proportion by weight comprised between 2% and 10%, more preferably between 3% and 6%, and yet more preferably 4%; propylene glycol in a proportion by weight comprised between 2% and 15%, preferably between 4% and 10%, and yet more preferably between 5% and 7%; carbomer in a proportion by weight comprised between 0.5% and 2%, preferably between 0.75% and 1.5%, and yet more preferably between 0.9% and 1.2%; triethanolamine in a proportion by weight comprised between 0.1% and 1%, preferably between 0.2% and 0.8%, and yet more preferably between 0.3% and 0.6%; and water in a proportion by weight comprised between 75% and 95%, more preferably between 80% and 92%, and yet more preferably between 85% and 90%.

In the composition of the invention, the sum of the percentages by weight of the components is 100%.

The pH of the gel is preferably comprised between 5.5 and 7.5, more preferably comprised between 6 and 6.5.

The phosphodiesterase inhibitor is preferably selected from the group consisting of a phosphodiesterase 1 (PDE1) inhibitor, a phosphodiesterase 3 (PDE3) inhibitor, a phosphodiesterase 4 (PDE4) inhibitor and a non-selective phosphodiesterase inhibitor, and a combination thereof; more preferably, the phosphodiesterase inhibitor is selected from the group consisting of pentoxifylline, rolipram, milrinone and ibudilast; yet more preferably, the phosphodiesterase inhibitor is pentoxifylline.

The authors of the present invention have observed that the administration of the phosphodiesterase inhibitor in the form of hydrophilic gel is particularly advantageous for the use of this invention, since said gel has the particularity that it is dissolved upon contacting the semen, as a result of the natural liquefaction process experienced by semen after being deposited in the vagina. Therefore, with a hydrophilic gel, sperm released from the mucilaginous layer of the semen can homogenously receive contact with the phosphodiesterase inhibitor in a particularly effective manner.

Optionally, the compositions for transvaginal application of the present invention can contain one or more additional excipients, for example, antioxidants, humectants, preservatives, thickeners, emollients, emulsifiers, pH-regulating agents, among others.

In the liquid or semi-solid compositions formulated using water as the carrier, a preservative is generally included. Preferred preservatives include parabens (methylparaben, ethylparaben, propylparaben, butylparaben), benzalkonium chloride, and benzyl alcohol. More preferably a combination of propylparaben and methylparaben is used.

Kit

A kit including the composition of the invention and instructions for administrating same is also part of the invention.

In a preferred embodiment, the kit includes three single-doses of phosphodiesterase inhibitor between 200 mg and 800 mg in each of them, preferably between 300 mg and 600 mg, more preferably between 350 mg and 450 mg, and yet more preferably 400 mg of phosphodiesterase inhibitor.

The phosphodiesterase inhibitor is preferably selected from the group consisting of a phosphodiesterase 1 (PDE1) inhibitor, a phosphodiesterase 3 (PDE3) inhibitor, a phosphodiesterase 4 (PDE4) inhibitor and a non-selective phosphodiesterase inhibitor, and a combination thereof; more preferably, the phosphodiesterase inhibitor is selected from the group consisting of pentoxifylline, rolipram, milrinone and ibudilast; yet more preferably, the phosphodiesterase inhibitor is pentoxifylline.

The following indications for self-administration are preferred: the couple must have sexual intercourse with vaginal ejaculation on the days of maximum fertility, and must introduce the gel in the vaginal cavity immediately after coitus with the applicator provided for such purpose, remaining in a supine position for at least one hour being advisable.

The most fertile days can be determined by means of using the methods common for that purpose, such as for example, cervical mucus test, vaginal ultrasound, or ovulation test.

Eventually, the composition of the invention can be administered simultaneously with an ovulation inducer.

The single-dose of the composition can be irrespectively administered in 3 different cycles or in several days of the same cycle.

The following examples below are described for the purpose of illustrating the invention, not for limiting same.

Example 1

In Vitro Assay of the Effect of Milrinone, Ibudilast and Pentoxifylline on Sperm Motility In each case the corresponding phosphodiesterase inhibitor (rolipram, milrinone, ibudilast and pentoxifylline) was dissolved in a commercial medium suitable for performing sperm preparations (SpermRinse®) to the desired concentration. The SpermRinse® solution consists of a bicarbonate and HEPES (N-2-(hydroxyethyl)piperazine-N'-ethanesulfonic acid) buffered medium containing human serum albumin.

A semen sample was taken from a patient with asthenozoospermia and it was kept at room temperature for 5 minutes after liquefaction, it was mixed with SpermRinse® solution without phosphodiesterase inhibitor in a volumetric ratio of 1:1.

Another part of the semen was mixed also after liquefaction with the SpermRinse® solution containing the phosphodiesterase inhibitor also in a proportion of 1:1 by volume.

For each observation, 3 microdrops of the preparation were used, they were placed under an optical microscope with 20× objective and Makler camera. A sperm count was performed, the number of type A sperm (advancing rapidly, with rectilinear trajectory) and type B sperm (advancing rapidly, with curvilinear trajectory) of each sample being counted. This was performed for the untreated sample and for the samples treated with the phosphodiesterase inhibitor. Three readings were made for each sample and the mean value was calculated.

Likewise, a subjective observation of the increase of sperm speed of all the sperm types was also performed for the samples treated with the phosphodiesterase inhibitor, with respect to the untreated samples.

The results are summarized in the following table:

| Product (concentration) | Increase in sperm type A + B | Increase in sperm speed |
|---|---|---|
| Pentoxifylline (1 μM) | ++ | ++ |
| Milrinone (1 μM) | ++ | ++ |
| Ibudilast (100 μM) | ++ | ++ |

Second column corresponds to the increase observed in fast sperm, the symbol ++ indicates an increase greater than 40% in the A+B sperm type count.

Third column corresponds to the increase in the individual speed of all the sperm types, the rating was subjectively assigned depending on the increase in the motility observed, such that the symbol ++ denotes a very significant increase in sperm motility.

Example 2

Preparation of a Pentoxifylline Gel for Transvaginal Administration

The following ingredients were used for preparing 400 g of gel:

| Ingredient | Weight/Volume |
|---|---|
| Pentoxifylline | 16 g |
| Carbomer 940 | 4 g |
| Propylene glycol | 20 ml |
| Water | q.s 400 g of gel |
| Triethanolamine | q.s pH (6-6.5) approx. 1.5-2 ml |
| Propylparaben | sufficient amount |
| Methylparaben | sufficient amount |

Water, propylene glycol and preservatives were introduced in a recipient with stirring. The mixture was kept under stirring until complete dissolution. Pentoxifylline was incorporated to the previous solution and stirred until completing the dissolution.

Carbomer was then incorporated under vigorous stirring and the mixture was left to settle for 24 h. After this time, the pH was adjusted with triethanolamine to a value comprised between 6 and 6.5.

The gel obtained had a pentoxifylline content of 4% by weight. This gel was packaged in a sterile tube type recipient which contained 10 g of gel and which was provided with a vaginal applicator.

Example 3

Assay of the Effectiveness of Pentoxifylline in the Treatment of Couples with Infertility The effectiveness of intravaginal administration of pentoxifylline in infertility treatment was assayed in a group of 20 couples selected according to the same criteria where the would have been susceptible to conjugal artificial insemination, i.e., they were unable to achieve pregnancy after at least a one year period of maintaining sexual relationships without protection, Three single-doses of pentoxifylline gel of 10 g each obtained according to the method described in Example 1 were administered to said couples with the following indications for self-administration: the couple must have sexual intercourse with vaginal ejaculation within the days of maximum fertility, and must introduce the gel in the vaginal cavity immediately after coitus with the applicator provided for such purpose, remaining in a supine position for at least one hour being advisable.

The most fertile days were determined by cervical mucus test, vaginal ultrasound, or ovulation test.

An ovulation inducer, clomiphene or purified human gonadotrofin, irrespectively, was simultaneously administered to 6 of the couples.

The gel was administered in 3 different cycles or in several days of the same cycle.

A meeting was conducted with the patients between 15 and 20 hours after each administration and a microscopic examination of the endocervical exudate was performed. It was observed in all cases that:

an improvement in sperm quality in terms of motility, both in cases of asthenozoospermia and in cases of normospermia.

a significant number of type A sperm according to the WHO classification.

an improvement in cervical mucus characteristics, in terms of its filancia, transparency and leukocytic diathesis.

Among the 20 couples transvaginally treated with pentoxifylline, 4 pregnancies were achieved, i.e., an effectiveness of 20%, which is significantly greater than that achieved by conjugal artificial insemination (14.7%).

Side effects due to the treatment were not observed in any case.

The invention claimed is:

1. A method of treating infertility in a subject in need thereof, comprising:
   administering an effective amount of a pharmaceutical composition comprising a phosphodiesterase inhibitor and at least one pharmaceutically acceptable excipient transvaginally to the subject before and/or after coitus, wherein the pharmaceutical composition is in the form of a gel, ointment or cream.

2. The method of claim 1, wherein the phosphodiesterase inhibitor is selected from the group consisting of a phosphodiesterase 1 (PDE1) inhibitor, a phosphodiesterase 3 (PDE3) inhibitor, a phosphodiesterase 4 (PDE4) inhibitor, a non-selective phosphodiesterase inhibitor, and combinations thereof.

3. The method of claim 2, wherein the phosphodiesterase inhibitor is selected from the group consisting of pentoxifylline, rolipram, milrinone and ibudilast.

4. The method of claim 3, wherein the phosphodiesterase inhibitor is pentoxifylline.

5. The method of claim 1, wherein the infertility is substantially caused by male infertility.

6. The method of claim 5, wherein the male infertility is due to anomalies in semen characteristics.

7. The method of claim 6, wherein the male infertility is due to asthenozoospermia.

8. The method of claim 1, wherein the phosphodiesterase inhibitor is administered in an amount between 200 mg and 800 mg in each administration.

9. The method of claim 1, wherein the method further comprises administering the phosphodiesterase inhibitor in combination with an ovulation-inducing drug comprising clomiphene, human gonadotropin, or human recombinant gonadotropin.

10. The method of claim 1, wherein the method further comprises administering the phosphodiesterase inhibitor as a complement to an artificial insemination technique.

11. The method of claim 1, wherein the pharmaceutical composition is in the form of a gel.

12. A method of treating infertility in a subject in need thereof, comprising:
   administering an effective amount of a pharmaceutical composition comprising pentoxifylline and at least one pharmaceutically acceptable excipient transvaginally to the subject before and/or after coitus, wherein the pharmaceutical composition is in the form of an ovule, vaginal suppository, vaginal tablet, cream, ointment, paste, gel or foam.

13. The method of claim 12, wherein the infertility is substantially caused by male infertility.

14. The method of claim 13, wherein the male infertility is due to anomalies in sperm characteristics.

15. The method of claim 14, wherein the male infertility is due to asthenozoospermia.

16. The method of claim 12, wherein the composition is in the form of a gel, ointment or cream.

17. The method of claim 16, wherein the composition is in the form of a gel.

18. The method of claim 12, wherein the pentoxifylline is administered in an amount between 200 mg and 800 mg in each administration.

19. The method of claim 12, wherein the method further comprises administering the pentoxifylline in combination with an ovulation-inducing drug comprising clomiphene, human gonadotropin, or human recombinant gonadotropin.

20. The method of claim 12, wherein the method further comprises administering the pentoxifylline as a complement to an artificial insemination technique.

21. A method of treating infertility in a subject in need thereof, comprising:
   administering an effective amount of a pharmaceutical composition comprising pentoxifylline and at least one pharmaceutically acceptable excipient transvaginally to the subject before and/or after coitus, wherein the pharmaceutical composition is in the form of an ovule, vaginal suppository, vaginal tablet, cream, ointment, paste, gel or foam, wherein the infertility is substantially caused by male infertility and wherein the male infertility is due to asthenozoospermia.

22. The method of claim 21, wherein the composition is in the form of a gel, ointment or cream.

23. The method of claim 22, wherein the composition is in the form of a gel.

24. The method of claim 21, wherein the pentoxifylline is administered in an amount between 200 mg and 800 mg in each administration.

25. The method of claim 21, wherein the method further comprises administering the pentoxifylline in combination with an ovulation-inducing drug comprising clomiphene, human gonadotropin, or human recombinant gonadotropin.

26. The method of claim 21, wherein the method further comprises administering the pentoxifylline as a complement to an artificial insemination technique.

\* \* \* \* \*